United States Patent [19]
Cotter et al.

[11] Patent Number: 5,919,822
[45] Date of Patent: Jul. 6, 1999

[54] USE OF SHORT CHAIN FATTY ACID CONTAINING LIPIDS TO MAINTAIN GASTROINTESTINAL INTEGRITY AND FUNCTION IN PATIENTS

[75] Inventors: Richard Cotter, Grand Rapids, Mich.; Hugh Tucker, Barrington, Ill.

[73] Assignee: Baxter International, Inc., Deerfield, Ill.

[21] Appl. No.: 07/831,627

[22] Filed: Feb. 6, 1992

Related U.S. Application Data

[63] Continuation of application No. 07/506,938, Apr. 10, 1990, abandoned.

[51] Int. Cl.$^6$ .......................... A61K 31/20; A61K 31/23; A61K 47/44; A61K 9/10
[52] U.S. Cl. .......................... 514/552; 514/558; 514/786; 514/937; 514/943
[58] Field of Search .................................. 514/552, 558, 514/937, 786, 943

[56] References Cited

U.S. PATENT DOCUMENTS

| | | | |
|---|---|---|---|
| 4,409,239 | 10/1983 | Yu | 404/305 |
| 4,526,793 | 7/1985 | Ingenbleek et al. | 426/602 |
| 4,528,197 | 7/1985 | Blackburn | 514/552 |
| 4,665,057 | 5/1987 | Nelson et al. | 514/552 |
| 4,678,807 | 7/1987 | Cotter et al. | 514/552 |
| 4,678,808 | 7/1987 | Ward et al. | 514/822 |
| 4,690,820 | 9/1987 | Simko | 514/552 |
| 4,703,062 | 10/1987 | Blackburn et al. | 514/552 |
| 4,735,967 | 4/1988 | Neesby | 514/557 |
| 4,753,963 | 6/1988 | Jandacek et al. | 514/552 |
| 4,810,726 | 3/1989 | Bistrian et al. | 514/552 |
| 4,920,098 | 4/1990 | Cotter et al. | 514/558 |
| 4,952,606 | 8/1990 | Babayan et al. | 514/552 |
| 4,992,292 | 2/1991 | Klemann et al. | 426/611 |

OTHER PUBLICATIONS

Johnson et al C.A. 107:235207Q (1987); Cotter et al C.A. 107:76708K (1987).
Guisard et al C.A. 74:1665K (1971); Maiz et al C.A. 101:190253J (1984).
Dawes et al C.A. 104:147650M (1986); Ekman et al C.A. 108:11038T (1988).
Lima et al C.A. 109:229346J (1988); Palacios et al C.A. 110:6836P (1989).
Lutz et al C.A. 110:211467K (1989); Hioki et al C.A. 111:56303D (1989).
Roessle et al C.A. 113:75428F (1990); Sobrado et al C.A. 103:213977F (1985).
Hamawy et al C.A. 103:213963Y (1985); Yamakawa et al C.A. 108:203699F (1988).
Koruda et al Gastroenterology 95:715–720 Effect of Parenteral Nutrition Supplemented with Short–Chain Fatty Acids on Adaption to Massive Small Bowel Resection, Sep. 1988.
McNeil Am. J. Clin. Nutr. 39(2):338–342 The Contribution of the Large Intestine to Energy Supplies in Man, Feb. 1984.
Roediger et al Digestive Diseases and Sciences 26(2):100–106 Effect of Short Chain Fatty Acid on Sodium Absorption in Isolated Human Colon Perfused Through the Vascular Bed, Feb. 1981.
Ruppin et al Gastroenterology 78(6):1500–1507 Absorption of Short Chain Fatty Acids by the Colon, Jun. 1980.
McNeil et al Gut(19):819–822 Short Chain Fatty Acid Absorption by the Human Large Intestine, 1978.
Schmitt et al Digestive Diseases and Sciences 22(Y):340–347 Absorption of Short Chain Fatty Acids from the Human Ileum, 1977.
Schmitt et al Gastroenterology 70(2):211–215 Absorption of Short Chain Fatty Acids from the Human Jejenum, 1976.
Bowling et al Lancet 342:1266–1268 Reversal by Short–Chain Fatty Acids of Colonic Fluid Secretion Induced by Enteral Feeding, Nov. 1993.
Koruda et al Am. Jl. Clinical Nutrition 51:685–689 Parenteral Nutrition Supplemented with Short Chain Fatty Acids: Effect on the Small Bowel Mucosa in Normal Rats, 1990.
Kripke et al Am. Jl. Clinical Nutrition 53(4):954–962 Experimental Short Bowel Syndrome: Effect of an Elemental Diet Supplemented with Short Chain Triglycerides, 1991.
Karlstad et al Am. Jl. Clinical Nutrition 55:1005–1011 Parenteral Nutrition with Short and Long Chain Triglycerides: Triacitin Reduces Atrophy of Small and Large Bowel Mucosa in Burned Rats, 1992.

(List continued on next page.)

*Primary Examiner*—Shep K. Rose
*Attorney, Agent, or Firm*—Hill & Simpson

[57] ABSTRACT

A method for the use of short chain fatty acids containing lipids in clinical nutrition to maintain gastrointestinal integrity and function in conditions where normal short chain fatty acid substrates, provided by bacterial fermentation of carbohydrates, is inadequate due to the clinical condition of the patient. By providing the short chain fatty acid in a lipid form of free fatty acid, triglyceride, diglyceride, monoglyceride, phospholipid, or cholesterol ester one is able to avoid the clinical defect and allow the gastrointestinal tract to continue to maintain its integrity and function. The short chain fatty acids of the present invention can be provided either in enteral preparations or parenteral preparations.

The short chain fatty acids can be provided by hydrolysis of a structure such as:

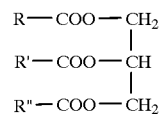

wherein R—COO—, R'—COO—, and R"—COO— represent either the same or different short chain fatty acids.

15 Claims, No Drawings

OTHER PUBLICATIONS

Mortensen et al Br. J. Surg. 78:1208–1211 Microcirculatory and Trophic Effects of Short Chain Fatty Acids in the Human Rectum After Hartmann's Procedure, Oct. 1991.

Scheppach et al Gastroenterology 103:51–56 Effect of Butyrate Enemas on the Colonic Mucosa in Distal Ulcerative Colitis, 1992.

Scheppach et al Jl. of Parenteral and Enteral Nutrition 16(1):43–48 Effect of Short Chain Fatty Acids on the Human Colonic Mucosa In Vitro, Feb. 1992.

Senegore et al Diseases of the Colon and Rectum 35(10):923–927 Short Chain Fatty Acid Enemas: A Cost-Effective Alternative in the Treatment Nonspecific Procto Sigmoiditis, Oct. 1992.

Komorowski Am. Jl. Surgical Pathology 14(6):548–554 Histologic Spectrum of Diversion Colitis, 1990.

Roediger Diseases of the Colon and Rectum 33:858–862 The Starved Colon–Diminished Mucosal Nutrition, Diminished Absorption and Colitis, Oct. 1990.

Brever et al Digestive Diseases and Sciences 36(2):185–187 Rectal Irrigation with Short Chain Fatty Acids for Distal Ulcerative Colitis, Feb. 1991.

Guillemot et al Diseases of the Colon and Rectum 34:861–864 Treatment of Diversion Colitis by Short Chain Fatty Acids, Oct. 1991.

Harig et al N. Engl. J. Med.(320)–:23–28 Treatment of Diversion Colitis with Short Chain Fatty Acid Irrigation, Jan. 1989.

Kriptke et al Jl. of Parenteral and Enteral Nutrition (13):109–116 Stimulation of Intestinal Mucosal Growth with Intracolonic Infusion of Short Chain Fatty Acids, Mar.–Apr. 1989.

Settle Jl. of Parenteral and Enteral Nutrition (12)(6):5104–5107 Short Chain Fatty Acids and Their Potential Role in Nutritional Support, Nov.–Dec. 1988.

Carlos et al Jl. of Parenteral and Enteral Nutrition (12)(6):598–5101 Short Chain Fatty Acids: Present Prospect–Future Alternative, Nov.–Dec. 1988.

Rolandelli et al, Effects of Intraluminal Infusion of Short–Chain Fatty Acids on the Healing of Colonic Anastomosis in the Rat, Surgery, vol. 100, No. 2, Aug. 1986, pp. 198–204.

Scheppach et al, Faecal Short–Chain Fatty Acids After Colonic Surgery, European Journal of Clinical Nutrition (1989) 43, pp. 21–25.

Koruda et al, Effect of Parenteral Nutrition Supplemented with Short–Chain Fatty Acids on Adaptation to Massive Small Bowel Resection, Gastroenterology, vol. 95, No. 3, Sep. 1988, pp. 715–720.

Kripke et al, Stimulation of Intestinal Mucosal Growth with Intracolonic Infusion of Short–Chain Fatty Acids, Journal of Parenteral and Enteral Nutrition, vol. 13, No. 2, Mar./Apr. 1989, pp. 109–116.

Harig et al, Treatment of Diversion Colitis with Short–Chain–Fatty Acid Irrigation, The New England Journal of Medicine, vol. 320, No. 1, Jan. 5, 1989, pp. 23–28.

Kvietys et al, Effect of Volatile Fatty Acids on Blood Flow and Oxygen Uptake by the Dog Colon, Gastroenterology, vol. 80, No. 5, Part 1, May 1981, pp. 962–969.

Rolandelli et al, A Comparison of Parenteral Nutrition and Enteral Feeding with Pectin in Experimental Colitis, Clinical Research, vol. 33, No. 2, 1985, p. 708A.

Rolandelli et al, The Effect of Enteral Feedings Supplemented with Pectin on the Healing of Colonic Anastomoses in the Rat, Surgery, vol. 99, No. 6, Jun. 1986, pp. 703–707.

USE OF SHORT CHAIN FATTY ACID CONTAINING LIPIDS TO MAINTAIN GASTROINTESTINAL INTEGRITY AND FUNCTION IN PATIENTS

This is a continuation of application Ser. No. 506,938, filed Apr. 10, 1990 abandoned.

BACKGROUND OF THE INVENTION

The present invention relates to the use of short chain fatty acids containing lipids in clinical nutrition.

Lipids containing fatty acids from 1 to 6 carbons in length, short chain fatty acids (SCFA), are known to be produced in the gastrointestinal tract, in particular in the colon. Short chain fatty acids include formic, acetic, propionic, butyric, isobutyric, pentanoic, isopentenoic, and caproic. Typically, the short chain fatty acids are produced by bacterial fermentation. The substrate for the production of short chain fatty acids by bacterial fermentation are carbohydrates that are generally fiber in nature.

The short chain fatty acids are used by the gastrointestinal mucosa as an energy substrate to maintain integrity and function. One method of providing gastrointestinal mucosa with short chain fatty acids is to utilize a dietary fiber which is converted by luminal microorganism digestion to fatty acids. Due to a variety of clinical reasons, the ability of the gastrointestinal mucosa to use short chain fatty acids as an energy source can be impaired.

When in the course of human disease or therapy, for disease, the bacteria flora of the gut is modified, reduced, or eliminated, its ability to provide short chain fatty acids as an energy substrate is impaired. There are a number of procedures, specifically with respect to hospitalized individuals that can greatly alter or eliminate the microflora of the gut. This can occur, for example, due to antibiotics, chemotherapy, or radiation. Furthermore, when the fiber intake of the patient is restricted, such as with some current elemental diets, there is no substrate for microorganism digestion even if the microflora are viable.

Because, in the above-identified conditions, short chain fatty acids cannot be used by the gastrointestinal tract as an energy substrate gastrointestinal integrity and function cannot be maintained.

SUMMARY OF THE INVENTION

The present invention provides a method for the use of short chain fatty acids containing lipids in clinical nutrition to maintain gastrointestinal integrity and function in conditions where normal short chain fatty acid (SCFA) substrates, provided by bacterial fermentation of carbohydrates, is inadequate due to the clinical condition of the patient. By providing the short chain fatty acid in a lipid form of free fatty acid, triglyceride, phospholipid, or cholesterol ester one is able to avoid the clinical defect and allow the gastrointestinal tract to continue to maintain its integrity and function. This is essential to good nutritional status, disease resistance, immune competence, and rapid recovery from the disease state.

The short chain fatty acids of the present invention can be provided either in enteral preparations administered by mouth, nasogastric, gastric, or jejunostomy tube. Additionally, the short chain fatty acids of the present invention can also be administered as a parenteral preparation by peripheral or central venous infusions. Additionally, the short chain fatty acids can be administered directly into the colon by enema.

The short chain fatty acids can be provided by hydrolysis of a triglyceride, diglyceride, or monoglyceride. For example, the short chain fatty acids can be provided by hydrolysis of a structure such as:

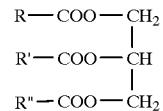

wherein R—COO—, R'—COO—, and R"—COO— represent either the same or different short chain fatty acids.

The short chain fatty acids can contain from two to six carbon chain lengths. Examples of the short chain fatty acids include acetic, proprionic, butyric, and caproic. The short chain fatty acids can also include valerate and isovalerate.

In an embodiment, the short chain fatty acids are provided in compositions including a fat content having a range of from approximately 12% to about 45% of the total caloric content (19 grams to 53 grams per 500 ml) of the composition. In an embodiment of the present invention, the short chain fatty acids comprise approximately 10% to about 50% of the total caloric percent of the fat content of the composition (1.9 grams to 26.5 grams per 500 ml). The remainder of the lipids can be made up of medium chain triglycerides and long chain triglycerides.

Additional features and advantages of the present invention are described in, and will be apparent from, the detailed description of the presently preferred embodiments.

DETAILED DESCRIPTION OF THE PRESENTLY PREFERRED EMBODIMENTS

The present invention provides a method for the use of short chain fatty acids containing lipids in clinical nutrition to maintain gastrointestinal integrity. The short chain fatty acids can be provided by a compound that upon hydrolysis yields short chain fatty acids. For example, the short chain fatty acids can be provided by hydrolysis of triglycerides, diglycerides, or monoglycerides.

The short chain fatty acids of the present invention can be provided as triacylglycerol for direct absorption by the gastrointestinal mucosa with intracellular hydrolysis to the short chain fatty acids and glycerol. The structure can be synthetically produced or derived from fractionation of butter or milk fat. The molecular structure can be as follows:

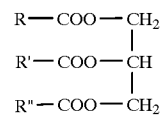

wherein R—COO, R'—COO, and R"—COO are either the same or different fatty acids.

The short chain fatty acids can contain from two to six carbon chain lengths. Examples of the short chain fatty acids include: acetic; proprionic; butyric; caproic; valerate; and isovalerate.

In an embodiment, the short chain fatty acids can be provided in compositions that include a fat content that ranges from approximately 12% to about 45% of the total caloric content (19 grams to 53 grams per 500 ml) of the composition. The short chain fatty acids preferably comprise approximately 10% to about 50% of the total caloric percent of the fat content (1.9 grams to 26.5 grams per 500 ml). The remainder of the lipid can be made up of medium chain triglycerides and long chain triglycerides.

The short chain fatty acids can be administered with a nutritional source including carbohydrates, vitamins, minerals, proteins, amino acids, and lipids.

The short chain fatty acids of the present invention can be administered either parenterally or enterally. As an enteral preparation, the short chain fatty acid composition can be administered by mouth, nasogastric, gastric, or jejunostomy tube. As a parenteral preparation, the short chain fatty acids of the present invention can be administered by peripheral or central venous infusions. The short chain fatty acids can also be administered directly into the colon by enema.

By way of example, and not limitation, formulations of the present invention including short chain fatty acids will now be given.

EXAMPLE 1

In an embodiment, an enteral formulation for tube feeding or oral feeding, pursuant to the present invention can have the composition set forth below. The formulation provides a complete liquid nutrition formula suitable for various clinical indications. The composition provides complete and balanced nutrients and therefore can be used as a supplement or a total feeding. The formulation is isotonic and has a low renal solute load, making it an ideal standard tube-feeding formula.

| NUTRIENT COMPOSITION | | per 250 ml AMOUNT |
|---|---|---|
| CALORIES | kcal | 250 |
| PROTEIN | g | 10 |
| (% of calories) | | (16%) |
| CARBOHYDRATE | g | 31.8 |
| (% of calories) | | (51%) |
| FAT | g | 9.5 |
| (% of calories) | | (33%) |
| SCFA | g | 1.9 |
| MCT | g | 3.6 |
| LCT | g | 4.0 |
| VITAMINS | | |
| VITAMIN A | IU | 940 |
| VITAMIN D | IU | 50 |
| VITAMIN E | IU | 5 |
| VITAMIN K | mcg | 31 |
| VITAMIN C | mg | 25 |
| THIAMINE ($B_1$) | mg | 0.38 |
| RIBOFLAVIN ($B_2$) | mg | 0.43 |
| NIACIN | mg | 5 |
| VITAMIN $B_6$ | mg | 0.75 |
| FOLIC ACID | mcg | 100 |
| PANTOTHENIC ACID | mg | 2.5 |
| VITAMIN $B_{12}$ | mcg | 1.5 |
| BIOTIN | mcg | 75 |
| CHOLINE | mg | 110 |
| MINERALS | | |
| SODIUM | mg | 125 |
| POTASSIUM | mg | 313 |
| CHLORIDE | mg | 250 |
| CALCIUM | mg | 125 |
| PHOSPHORUS | mg | 125 |
| MAGNESIUM | mg | 62.5 |
| IRON | mg | 2.3 |
| IODINE | mcg | 19 |
| COPPER | mg | 0.25 |
| ZINC | mg | 2.5 |
| MANGANESE | mg | 0.5 |

EXAMPLE 2

In an embodiment, an enteral formulation for tube feeding or oral feeding, pursuant to the present invention, can have the formulation set forth below. The formulation provides a nutritionally complete and high caloric liquid nutrition composition, indicated when increased calories are needed in a concentrated form. Low osmolality allows the formulation to be used as a tube feeding.

| NUTRIENT COMPOSITION | | per 250 ml AMOUNT |
|---|---|---|
| CALORIES | kcal | 375 |
| PROTEIN | g | 15 |
| (% of calories) | | (16%) |
| CARBOHYDRATE | g | 42.5 |
| (% of calories) | | (45%) |
| FAT | g | 16.9 |
| (% of calories) | | (39%) |
| SCFA | g | 5.0 |
| MCT | g | 5.9 |
| LCT | g | 6.0 |
| VITAMINS | | |
| VITAMIN A | IU | 1400 |
| VITAMIN D | IU | 75 |
| VITAMIN E | IU | 7.5 |
| VITAMIN K | mcg | 47 |
| VITAMIN C | mg | 38 |
| THIAMINE ($B_1$) | mg | 0.56 |
| RIBOFLAVIN ($B_2$) | mg | 0.64 |
| NIACIN | mg | 7.5 |
| VITAMIN $B_6$ | mg | 1.1 |
| FOLIC ACID | mcg | 150 |
| PANTOTHENIC ACID | mg | 3.8 |
| VITAMIN $B_{12}$ | mcg | 2.3 |
| BIOTIN | mcg | 110 |
| CHOLINE | mg | 170 |
| MINERALS | | |
| SODIUM | mg | 188 |
| POTASSIUM | mg | 470 |
| CHLORIDE | mg | 375 |
| CALCIUM | mg | 188 |
| PHOSPHORUS | mg | 188 |
| MAGNESIUM | mg | 94 |
| IRON | mg | 3.4 |
| IODINE | mcg | 28 |
| COPPER | mg | 0.38 |
| ZINC | mg | 3.8 |
| MANGANESE | mg | 0.75 |

EXAMPLE 3

In an embodiment, an enteral formulation for tube feeding or oral feeding, pursuant to the present invention, can have the formulation set forth below. The formulation provides a complete and balanced enteral formula that can be used as a tube or oral feeding and is indicated for severe fluid restriction or extremely high caloric requirements.

| NUTRIENT COMPOSITION | | per 250 ml AMOUNT |
|---|---|---|
| CALORIES | kcal | 500 |
| PROTEIN | g | 20 |
| (% of calories) | | (16%) |
| CARBOHYDRATE | g | 49 |
| (% of calories) | | (39%) |
| FAT | g | 26.5 |
| (% of calories) | | (45%) |
| SCFA | g | 13.0 |
| MCT | g | 6.0 |
| LCT | g | 7.5 |
| VITAMINS | | |
| VITAMIN A | IU | 1900 |
| VITAMIN D | IU | 100 |
| VITAMIN E | IU | 10 |
| VITAMIN K | mcg | 63 |
| VITAMIN C | mg | 50 |
| THIAMINE ($B_1$) | mg | 0.75 |
| RIBOFLAVIN (B2) | mg | 0.85 |
| NIACIN | mg | 10 |

-continued

| NUTRIENT COMPOSITION | | per 250 ml AMOUNT |
|---|---|---|
| VITAMIN B$_6$ | mg | 1.5 |
| FOLIC ACID | mcg | 200 |
| PANTOTHENIC ACID | mg | 5 |
| VITAMIN B$_{12}$ | mcg | 3 |
| BIOTIN | mcg | 150 |
| CHOLINE | mg | 230 |
| MINERALS | | |
| SODIUM | mg | 250 |
| POTASSIUM | mg | 625 |
| CHLORIDE | mg | 500 |
| CALCIUM | mg | 250 |
| PHOSPHORUS | mg | 250 |
| MAGNESIUM | mg | 125 |
| IRON | mg | 4.5 |
| IODINE | mcg | 38 |
| COPPER | mg | 0.5 |
| ZINC | mg | 5 |
| MANGANESE | mg | 1 |

EXAMPLE 4

In an embodiment, a liquid, isotonic, complete elemental diet including short chain fatty acids, pursuant to the present invention, can have the following composition. The composition provides an easily digested formula.

| NUTRIENT COMPOSITION | | per 500 ml AMOUNT |
|---|---|---|
| CALORIES | kcal | 500 |
| PROTEIN | g | 20.0 |
| CARBOHYDRATE | g | 63.5 |
| FAT*** | g | 19.5 |
| SCFA | g | 6.5 |
| MCT | g | 7.0 |
| LCT | g | 6.0 |
| Vitamin Composition | | |
| VITAMIN A | IU | 1875 |
| VITAMIN D | IU | 100 |
| VITAMIN E | IU | 10 |
| VITAMIN K | mcg | 62.5 |
| VITAMIN C | mg | 50 |
| THIAMINE (B$_1$) | mg | 0.75 |
| RIBOFLAVIN (B$_2$) | mg | 0.85 |
| NIACIN | mg | 10 |
| VITAMIN B$_6$ | mg | 1.5 |
| FOLIC ACID | mcg | 200 |
| PANTOTHENIC ACID | mg | 5 |
| VITAMIN B$_{12}$ | mcg | 3 |
| BIOTIN | mcg | 150 |
| CHOLINE | mg | 225 |
| SODIUM | mg | 250 |
| POTASSIUM | mg | 625 |
| CHLORIDE | mg | 500 |
| CALCIUM | mg | 300 |
| PHOSPHORUS | mg | 250 |
| MAGNESIUM | mg | 150 |
| IRON | mg | 4.5 |
| IODINE | mcg | 37.5 |
| COPPER | mg | 0.5 |
| ZINC | mg | 5.0 |
| MANGANESE | mg | 1.0 |

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. A method for maintaining gastrointestinal integrity and function in a patient whose gut bacteria flora is modified, reduced, or eliminated so as to impair its ability to provide short chain fatty acids from fiber as an energy source comprising:
    administering to the patient a composition including at least one lipid source chosen from the group consisting of triglycerides, diglycerides and monoglycerides that upon hydrolysis yields short chain fatty acids.

2. The method of claim 1 wherein the short chain fatty acids include at least one fatty acid chosen from the group consisting of: acetic; proprionic; butyric; caproic; valerate; and isovalerate.

3. The method of claim 1 wherein the composition is administered enterally.

4. The method of claim 1 wherein the composition is administered parenterally.

5. The method of claim 1 wherein the short chain fatty acids comprise approximately 1.2% to about 22.5% of the total caloric content of the composition.

6. A method for maintaining gastrointestinal integrity and function in a patient whose gut bacterial flora is modified, reduced, or eliminated so as to impair its ability to provide short chain fatty acids from fiber as an energy source comprising:
    administering to the patient a composition including a lipid source having an emulsion of triglycerides that upon hydrolysis yield short chain fatty acids.

7. A method for maintaining gastrointestinal integrity and function in a patient whose gut bacteria flora is modified, reduced, or eliminated so as to impair its ability to provide short chain fatty acids from fiber as an energy source comprising:
    administering to the patient a composition including a lipid source, the lipid source including a short chain fatty acid source having the structure:

$$\begin{array}{l} R-COO-CH_2 \\ \quad\quad\quad\quad\quad | \\ R'-COO-CH_2 \\ \quad\quad\quad\quad\quad | \\ R''-COO-CH_2 \end{array}$$

wherein: R—COO—, R'—COO—, and R"—COO— are fatty acids having two to six carbon lengths.

8. The method of claim 7 wherein the composition is administered enterally.

9. The method of claim 7 wherein the composition is administered parenterally.

10. The method of claim 7 wherein the short chain fatty acid source comprises approximately 1.2% to about 22.5% of the total caloric content of the composition.

11. The method of claim 7 wherein the lipid source comprises approximately 12% to about 45% of the total caloric content of the composition.

12. The method of claim 7 wherein upon hydrolysis, the short chain fatty acid source yields at least one fatty acid chosen from the group consisting of: acetic; proprionic; butyric; caproic; valerate; and isovalerate.

13. The method of claim 7 wherein the composition includes a protein source, and a carbohydrate source.

14. The method of claim 13 wherein the composition includes at least one vitamin source and at least one mineral source.

15. The method of claim 7 wherein the lipid source includes a source of medium chain triglycerides and long chain triglycerides.

* * * * *